United States Patent [19]

Gubelmann et al.

[11] Patent Number: 5,082,978

[45] Date of Patent: Jan. 21, 1992

[54] SELECTIVE MONOMETHYLATION OF PHENOLIC COMPOUNDS

[75] Inventors: Michel Gubelmann, Lyon; Christian Allandrieu, Villeurbanne, both of France

[73] Assignee: Rhone-Poulenc Chimie, Courbevoie, France

[21] Appl. No.: 701,347

[22] Filed: May 9, 1991

Related U.S. Application Data

[63] Continuation of Ser. No. 390,069, Aug. 7, 1989, abandoned.

[30] Foreign Application Priority Data

Aug. 5, 1988 [FR] France ............................ 88 10812

[51] Int. Cl.$^5$ ............................................. C07C 41/00
[52] U.S. Cl. ..................... 568/637; 568/636; 568/638; 568/643; 568/648; 568/649; 568/650; 568/651; 568/652
[58] Field of Search ............... 568/637, 638, 636, 643, 568/648, 649, 650, 651, 652

[56] References Cited

U.S. PATENT DOCUMENTS

| | | |
|---|---|---|
| 2,697,732 | 12/1954 | Mavity . |
| 2,909,568 | 10/1959 | Gleim ................................. 568/651 |
| 3,895,076 | 7/1975 | Bauer et al. ......................... 568/652 |
| 4,307,253 | 12/1981 | Neumann et al. ................... 568/630 |
| 4,487,975 | 12/1984 | Ratton ................................. 568/637 |
| 4,654,446 | 3/1987 | Brunelli et al. ..................... 568/648 |

FOREIGN PATENT DOCUMENTS 825487 4/1981 U.S.S.R. .

OTHER PUBLICATIONS

Chemical Abstracts, vol. 106, No. 19, 11 Mai 1987, p. 617, Resume No. 155658b, Columbus, Ohio, U.S.; P. Beltrame et al.: "Methyl Transfer from Anisole to Phenol on HY Zeolite", Gazz. Chem. Ital. 1986 116(8), 473-4.

Primary Examiner—Bruce Gray
Attorney, Agent, or Firm—Burns, Doane, Swecker & Mathis

[57] ABSTRACT

Mono-, di- and triphenols are selectively monomethylated by reaction with para-dimethoxybenzene in the presence of a catalytically effective amount of an acid catalyst.

12 Claims, No Drawings

SELECTIVE MONOMETHYLATION OF PHENOLIC COMPOUNDS

This application is a continuation of application Ser. No. 07/390,069, filed Aug. 7, 1989 now abandoned.

BACKGROUND OF THE INVENTION

1. Field of the Invention

The present invention relates to the monomethylation of phenolic compounds.

2. Description of the Prior Art

Phenolic compounds (mono-, di- or triphenols) in which one of the phenol functions is methylated, namely, is replaced by a methoxy (—OCH$_3$) group, are known useful intermediates for a wide variety of organic syntheses. The preparation of such intermediates from phenolic compounds mandates the availability of suitable reactants capable of methylating the phenolic function, and suitable reaction conditions for said reactants, in order to selectively produce, i.e., without co-production of unwanted by-products in too large of amounts, the desired final products. In addition, specifically as regards the chemistry of the diphenolic compounds, para-dimethoxybenzene is prepared as a by-product, and need exists to enhance the commercial worth of this particular compound.

SUMMARY OF THE INVENTION

Accordingly, a major object of the present invention is the provision of a process for the selective methylation of a phenol group utilizing para-dimethoxybenzene.

Briefly, the present invention features the selective methylation of phenol groups by reacting paradimethoxybenzene with a phenolic compound having the formula:

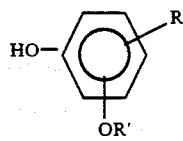
(I)

in which R is H, OH, alkyl, alkoxy, halogen, phenyl, alkyl-substituted phenyl or CF$_3$; and R' is H, alkyl, C$_6$H$_4$OH or C$_6$H$_4$O-alkyl.

DETAILED DESCRIPTION OF THE PREFERRED EMBODIMENTS OF THE INVENTION

More particularly according to the present invention, by the term "alkyl" is intended a saturated linear or branched chain alkyl radical having from 1 to 4 carbon atoms.

The most commercially important phenolic compounds of formula (I) are the diphenols, i.e., those compounds in which R is H and R' is H, the OH group therefore being situated in the ortho- or para-position with respect to the other OH group.

The reaction scheme according to the invention may thus be represented:

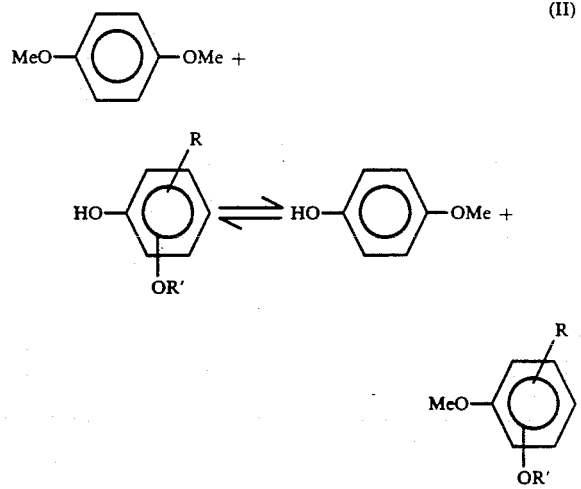

in which Me is a methyl group; and R and R' are as defined above.

Reaction (II) is an equilibrated reaction; its yield of the desired final product can therefore depend on the relative amounts of reactants used. Advantageously, and in particular on an industrial scale, the optimal amounts of reactants will be used, taking account of the kinetics of the reaction, the equilibrium, the cost of the products and also possible secondary reactions.

The reaction according to the invention is carried out in the presence of a catalyst which is any acid, and in particular the solid acids having acid functions conforming to the definitions of Lewis or Bronsted acids. The acids used may therefore be liquid (H$_2$SO$_4$ for example) or solid. The solid catalysts, which constitute the preferred catalysts of the invention, may be described as all solids having a cation exchange capacity which has been partly or completely exchanged by H$^+$ and/or a Lewis acid (derived from an element of valence $\geq$ 3). Exemplary of such solid catalysts, particularly representative are:

(i) clays which have been treated with a strong acid;
(ii) zeolites which have also been subjected to exchange with strong acids, or which have been produced in known manner by decomposition of ammonium salts of the corresponding ammoniated zeolites;
(iii) macro-crosslinked and sulfonated resins of the styrene-divinylbenzene type;
(iv) acid or amphoteric oxides, the acid activity of which can advantageously be increased by treatment with an acid; and
(v) heteropolyacids, such as phosphomolybdic or phosphovanadic acids, and the like.

The reaction conditions of course depend, on the one hand, on the reactants and, on the other, on the catalysts.

The reaction temperature advantageously ranges from 80° to 400° C., but, preferably, temperatures ranging from 150° to 250° C. will be used.

The reaction medium may comprise a liquid which is inert at the temperatures used; this is the case, in particular (but not intended to be limiting), when a liquid catalyst is used. When a solid catalyst is used, the reaction may preferably be carried out by simply contacting the said catalyst and the reactants, which are then gaseous, at the selected temperature. Of course, it will most often be necessary, taking into account the boiling temperature of the reactants and the temperature selected for the reaction, to conduct the operation under pressure.

The relative proportions of the reactants to be used may be varied to take into account, in particular as explained above, the fact that the desired reaction is equilibrated. However, because the present invention essentially features methylation of a single phenol function of the phenolic compound, the reactants (dimethoxybenzene and phenolic compound) will preferably be used in approximately equimolecular amounts.

The amounts of catalyst to be used essentially depend on the activity of the catalyst, which activity is directly proportional to the ion exchange capacity of the catalyst.

When a liquid acid is used, for example sulfuric acid, the exchange capacity of which is 20 meq./g (meq.=milliequivalent), preferably 0.05 to 0.5 g concentrated acid will be used per 5 to 50 mmol of para-dimethoxybenzene.

When, for example, a solid catalyst having an exchange capacity of 0.5 to 1.5 meq./g is used, about 1 g of this catalyst will be used per 5 to 50 mmol of paradimethoxybenzene.

By carrying out the process of the invention as described above, there are simultaneously attained a good degree of conversion of the two reactants and an increased selectivity with respect to the desired final product, i.e., a phenolic compound in which one of the phenolic functions has been methylated. The degree of conversion of each of the reactants is generally on the order of 20% to 80% and the selectivity for the desired final product is generally on the order of 60% to 95%.

In order to further illustrate the present invention and the advantages thereof, the following specific examples are given, it being understood that same are intended only as illustrative and in nowise limitative.

EXAMPLE 1

1 g of a commercial zeolite of the faujasite type (US-Y from TOYO-SODA), 2.5 g (namely, 22.7 mmol) hydroquinone (HQ) and 3.1 g (namely, 21.7 mmol) para-dimethoxybenzene (PDMB) were introduced into a glass tube. After sealing, the tube was inserted into a metallic sheath which was placed in a balancing furnace (known to the art as a CARIUS furnace). The temperature of the furnace was increased to 200° C. for 2.5 hours.

Upon completion of the reaction, the tube/sheath assembly was cooled and the tube was removed from its sheath and opened. The solid catalyst was recovered by filtration on fritted glass and washed with ethyl acetate. Ethyl acetate was added to the filtrate and the washing liquid to provide a volume of 100 ml. The resulting liquid mixture was analyzed by gas phase chromatography and the nature of the final products was confirmed by mass spectrometry.

The degree of conversion (DC), i.e., the percentage of the starting reactants which had been consumed was:
 (a) for hydroquinone (HQ) 54%
 (b) for para-dimethoxybenzene (PDMB) 58%.

The selectivity of the reaction (YD), defined as the number of moles of final product (para-methoxyphenol) produced with respect to the number of moles of starting reactant converted, was 77%.

EXAMPLE 2

The procedure of Example 1 was repeated, but using a commercial acid clay (Montmorillonite-KSF from Süd-Chemie, Munich-FRD) as the catalyst.
 DC (HQ)=53%
 DC (PDMB)=69%
 YD (PMP)=65%.

EXAMPLE 3

The procedure of Example 1 was repeated, but using pyrocatechol (PC) in place of the hydroquinone.
 DC (PC)=34%
 DC (PDMB)=48%
 YD (OMP)=53%
  (where: OMP=ortho-methoxyphenol)
 YD (PMP)=59%.

EXAMPLE 4

The procedure of Example 2 was repeated, but using pyrocatechol in place of the hydroquinone.
 DC (PC)=35%
 DC (PDMB)=59%
 YD (OMP)=73%
 YD (PMP)=70%.

EXAMPLE 5

This example (together with Examples 6 to 9) illustrates carrying out the process of the invention using a solid catalyst and conducting the reaction at atmospheric pressure.

3.2 g (23.2 mmol) PDMB, 2.5 g (22.7 mmol) HQ and 1 g of a commercial acid clay (TONSIL OPTIMUM FF from Sud-Chemie, Munich-FRD) were introduced into a 30 cm³ cylindrical glass reactor provided with magnetic stirring and a refrigerant. This mixture was heated at 170° C. for 3 hours with thorough stirring. The solid acid was recovered by filtration on fritted glass and washed with ethyl acetate. All of the organic products were determined by gas phase chromatography. Their nature was confirmed by mass spectrometry.
 DC (PDMB)=31%
 DC (HQ)=38%
 YD (PMP)=60%.

EXAMPLES 6 TO 9

The procedure of Example 5 was repeated, but under the following conditions:

| (i) | Charge | PDMB | 0.6 g; 4.4 mmol |
| | | HQ | 5.1 g; 46.4 mmol |
| | | catalyst | 0.5–1.0 g |
| (ii) | Temperature | 170° C. | |
| (iii) | Time | 1–3 hours. | |

The conditions employed (selection of catalyst; amount of catalyst used; reaction time) and the results obtained are reported in Table I.

TABLE I

| Example | Acid solid Type | Weight (g) | Time (h) | DC PDMB (%) | DC HQ (%) | YD PMP (%) |
|---|---|---|---|---|---|---|
| 6 | KSF clay | 1 | 3 | 64 | 45 | 76 |
| 7 | KSF clay | 1 | 1 | 39 | 27 | 92 |
| 8 | NAFION 117-H | 1 | 1 | 78 | 41 | 59 |
| 9 | NAFION 117-H | 0.5 | 1 | 63 | 28 | 59 |

NAFION, marketed by E.I. DUPONT DE NEMOURS, is a perfluorinated polymer of the general formula:

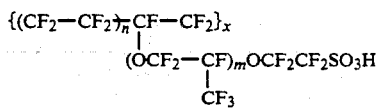

in which n is a number ranging from 5 to 13.5; m is an integer equal to 1, 2, or 3; and x has a value of about 1,000.

These polymers have acid ion exchange properties, and NAFION 117-H has an exchange capacity of 0.9 meq./g dry solid.

EXAMPLES 10 AND 11

Examples 10 and 11 illustrate carrying out the process according to the invention using a solid catalyst, at atmospheric pressure and in the presence of a co-solvent.

The procedure of Example 5 was repeated, but under the following conditions:

| (i) | Charge | PDMB | 2.6 g (18.8 mmol) |
|---|---|---|---|
| | | HQ | 2.2 g (20 mmol) |
| | | catalyst | 1 g of acid clay |
| | | (TONSIL OPTIMUM FF marketed by Sud-Chemie) | |
| | | co-solvent | 1.5 g |
| (ii) | Temperature | 200° C. | |
| (iii) | Reaction time | 2 hours. | |

In a comparative experiment carried out under the same conditions, with the same reactants, but in the absence of catalyst and co-solvent, the following results were obtained:
DC (PDMB)=2%
DC (HQ)=3%
YD (PMP)=0%.

The results obtained using either mesitylene or ortho-dichlorobenzene (ODCB) as solvent are reported in Table II:

TABLE II

| Example | Co-solvent | DC PDMB (%) | DC HQ (%) | YD PMP (%) |
|---|---|---|---|---|
| 10 | mesitylene | 30 | 43 | 70 |
| 11 | ODCB | 30 | 43 | 70 |

EXAMPLES 12 TO 14

These examples illustrate the use of a liquid catalyst, which was concentrated sulfuric acid.

The procedure was as in Examples 10 and 11, but replacing the clay with 0.15 g concentrated (98%) sulfuric acid; a co-solvent was also used, which was either mesitylene (Example 12), diethylene glycol dimethyl ether (Example 13, diglyme), or ortho-dichlorobenzene (ODCB).

The results are reported in Table III.

TABLE III

| Example | Co-solvent | DC PDMB (%) | DC HQ (%) | YD PMP (%) |
|---|---|---|---|---|
| 12 | mesitylene | 45 | 62 | 70 |
| 13 | diglyme | 27 | 73 | <100 |
| 14 | ODCB | 58 | 74 | 57 |

EXAMPLES 15–16

A liquid acid catalyst may also be used without the addition of co-solvent; this is illustrated in Examples 15 and 16.

The procedure was as in Example 5, under the following conditions:

| (i) | Charge | PDMB | 3.2 g |
|---|---|---|---|
| | | HQ | 2.5 g |
| | | liquid catalyst | 0.1 g |
| (ii) | Temperature | 170° C. | |
| (iii) | Time | 3 hours. | |

The results obtained using 98% $H_2SO_4$ and $F_3CSO_3H$ are reported in Table IV.

TABLE IV

| Example | Liquid acid | DC PDMB (%) | DC HQ (%) | YD PMP (%) |
|---|---|---|---|---|
| 15 | $H_2SO_4$ 98% | 38 | 53 | 63 |
| 16 | $F_3CSO_3H$ | 78 | 79 | 27 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the monomethylation of a phenolic compound, comprising reacting as the sole alkylation agent para-dimethoxybenzene with a phenol of the formula:

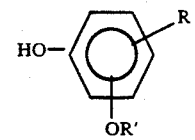

in which R is H, OH, alkyl, alkoxy, halogen, phenyl, alkyl-substituted phenyl, or $CF_3$, and R' is H, alkyl, $C_6H_4OH$ or $C_6H_4O$-alkyl, in the presence of a catalytically effective amount of an acid catalyst.

2. The process as defined by claim 1, said acid catalyst comprising a liquid acid.

3. The process as defined by claim 2, said liquid acid comprising sulfuric acid.

4. The process as defined by claim 1, said acid catalyst comprising solids having cation exchange capacity.

5. The process as defined by claim 1, comprising reacting equimolecular amounts of said phenol of formula (I) with para-dimethoxybenzene at a temperature ranging from about 80° C. to about 400° C.

6. The process as defined by claim 5, carried out at a temperature ranging from 150° C. to 250° C.

7. The process as defined by claim 1, wherein said phenol of formula (I), R and R' are H and OR' is in a position ortho- or para- with respect to the OH group.

8. The process as defined by claim 2, carried out in the presence of 0.05 g to 0.5 g of concentrated acid per 5 mmol to 50 mmol of para-dimethoxybenzene.

9. The process as defined by claim 4, carried out in the presence of 1 g of solid catalyst having an exchange capacity of 0.5 milliequivalent/g to 1.5 milliequivalent/g per 5 mmol to 50 mmol of para-dimethoxybenzene.

10. The process as defined by claim 1, carried out in an inert liquid reaction medium.

11. The process as defined by claim 4, said solid catalyst comprising a Lewis or Bronsted acid.

12. The process as defined by claim 4, said solid catalyst comprising a clay, zeolite, cation exchange resin, oxide or heteropolyacid.

* * * * *